(12) United States Patent
Tee

(10) Patent No.: US 11,430,570 B2
(45) Date of Patent: Aug. 30, 2022

(54) SYSTEM AND METHOD FOR MOBILE PLATFORM DESIGNED FOR DIGITAL HEALTH MANAGEMENT AND SUPPORT FOR REMOTE PATIENT MONITORING

(71) Applicant: Lai King Tee, San Jose, CA (US)

(72) Inventor: Lai King Tee, San Jose, CA (US)

(73) Assignee: Lai King Yee, San Jose, CA (US)

( * ) Notice: Subject to any disclaimer, the term of this patent is extended or adjusted under 35 U.S.C. 154(b) by 475 days.

(21) Appl. No.: 15/337,686

(22) Filed: Oct. 28, 2016

(65) Prior Publication Data

US 2017/0124276 A1    May 4, 2017

Related U.S. Application Data

(60) Provisional application No. 62/311,922, filed on Mar. 23, 2016, provisional application No. 62/248,251, filed on Oct. 29, 2015.

(51) Int. Cl.
*G16H 40/67* (2018.01)
*G08B 21/04* (2006.01)
(Continued)

(52) U.S. Cl.
CPC .......... *G16H 40/67* (2018.01); *A61B 5/0022* (2013.01); *G06F 21/6245* (2013.01);
(Continued)

(58) Field of Classification Search
CPC ............ G06F 19/3418; G06F 21/6245; G08B 21/0453; G08B 21/0446; G08B 21/043; G08B 21/24; G16H 40/67; G16H 10/60; G16H 80/00; A61B 5/0022; A61B 5/746; A61B 5/0205; A61B 5/1112;
(Continued)

(56) References Cited

U.S. PATENT DOCUMENTS

2009/0054737 A1*  2/2009  Magar .................. A61B 5/0205
                                                 600/300
2012/0050048 A1*  3/2012  Sandra .................... G01S 19/17
                                                 340/573.4
(Continued)

FOREIGN PATENT DOCUMENTS

WO    WO-2011044303 A2 *   4/2011   ............. G16H 40/67

OTHER PUBLICATIONS

Szczepański et al., A Mobile Device System for Early Warning of ECG Anomalies, Jun. 20, 2014, Sensors, pp. 11031-11044. (Year: 2014).*

*Primary Examiner* — Christopher L Gilligan
(74) *Attorney, Agent, or Firm* — Mark Koo; Gregory Carson; Lyman Moulton

(57) ABSTRACT

A mobile application is used for monitoring and management of users or patients with various health or disease conditions. Software system provides a platform with which the medical histories, the recent conditions and real-time measurement data for the patient can be organized and shared among various people who are involved in the caring of the patient. In addition to data sharing in a secured, private networking environment, the platform integrates the essential functions for people in the various caregivers' groups to communicate with each other in real-time so as to collaborate on the caring of the patient.

26 Claims, 9 Drawing Sheets

(51) Int. Cl.
  *G16H 10/60* (2018.01)
  *G06F 21/62* (2013.01)
  *G08B 21/24* (2006.01)
  *A61B 5/00* (2006.01)
  *A61B 5/0205* (2006.01)
  *A61B 5/11* (2006.01)
  *A61B 5/024* (2006.01)
  *A61B 5/01* (2006.01)
  *A61B 5/145* (2006.01)

(52) U.S. Cl.
  CPC ..... *G08B 21/0446* (2013.01); *G08B 21/0453* (2013.01); *G16H 10/60* (2018.01); *A61B 5/01* (2013.01); *A61B 5/0205* (2013.01); *A61B 5/02438* (2013.01); *A61B 5/1112* (2013.01); *A61B 5/1118* (2013.01); *A61B 5/14542* (2013.01); *A61B 5/746* (2013.01); *G08B 21/043* (2013.01); *G08B 21/24* (2013.01)

(58) Field of Classification Search
  CPC ..... A61B 5/02438; A61B 5/1118; A61B 5/01; A61B 5/14542
  See application file for complete search history.

(56) References Cited

U.S. PATENT DOCUMENTS

| | | | |
|---|---|---|---|
| 2012/0083669 A1* | 4/2012 | Abujbara | G06F 19/3475 600/300 |
| 2012/0220835 A1* | 8/2012 | Chung | A61B 5/0022 600/301 |
| 2013/0262155 A1* | 10/2013 | Hinkamp | G06Q 10/109 705/4 |
| 2014/0088994 A1* | 3/2014 | Kroh | G06F 19/00 705/2 |
| 2014/0180719 A1* | 6/2014 | Bell | G16H 80/00 705/3 |
| 2014/0188874 A1* | 7/2014 | Stivoric | G06F 16/24575 707/736 |
| 2014/0207486 A1* | 7/2014 | Carty | G06Q 10/10 705/2 |
| 2014/0249854 A1* | 9/2014 | Moore | G16H 15/00 705/3 |
| 2015/0205921 A1* | 7/2015 | Dick | G06F 19/00 705/2 |
| 2015/0242585 A1* | 8/2015 | Spiegel | G16H 10/60 705/2 |

* cited by examiner

| Date | Day of Week | Activity Description (walking/standing) | Start time | Stop / Resting time | Time – Back pain experienced | Time – Hip Pain experienced | Time – Pain experienced at other parts of the body | Notes / Meals |
|---|---|---|---|---|---|---|---|---|
| 3/21/2016 | Mon | | | | | | | |
| | | | | | | | | |
| | | | | | | | | |
| | | | | | | | | |

SYSTEM AND METHOD FOR MOBILE PLATFORM DESIGNED FOR DIGITAL HEALTH MANAGEMENT AND SUPPORT FOR REMOTE PATIENT MONITORING

CROSS REFERENCE TO RELATED APPLICATIONS

The present application claims priority from Provisional Patent Application No. 62/248,251 filed on Oct. 29, 2015 and Provisional Patent Application No. 62/311,922 filed on Mar. 23, 2016, which are incorporated herein by reference in its entirety.

BACKGROUND

The mobile phone users may have a basic feature phone for simple voice calls and text messaging. Smartphone technology could be costly and quite complex for some users, e.g. elderly with little education or patients with serious conditions. The software system is designed to avoid those constraints through the connections between the patients and their caregivers. It would support collaborations in the care of a patient by multiple people in the same group or across different groups, including but not limited to: Family members, Relatives, Neighbors, Friends, Personal nurses, Household helpers, Nursing homes, and Professional care teams (i.e. providers, nurses, doctors and specialists).

For patients who may not have access or capability to use the mHealth Application (App) on the smartphone themselves, their caregivers, e.g. some of those in one or more of the groups as listed above, who are "connected" to them, would be able to use the App to "monitor" and "manage" their "diseases" and "health status", "taking appropriate actions depending on the conditions".

For patients who are able to use the mHealth App on their smartphones, they would be able to use it to communicate with others who are connected with them via the App, e.g. to chat (voice, video or text) about their conditions, get advice and attention from their caregivers etc.

The platform supports the creation of personal health (medical) records, with configurable options for sharing and maintenance by selected individuals who are connected to the patient/user. The patient's health record on the phone can be updated manually or automatically through physiological or biosensors worn by the patients, and/or environmental sensors. The updates could be visible to the closest (first-level) caregivers who are connected to the patient via the App.

SUMMARY OF THE INVENTION

Based on the proliferation of mobile devices, a family/group-centric mobile health platform could be used as a tool for the mobile users to monitor and manage the health conditions of their family members. Using this platform, family members can store and organize the health data for each family member, which enables them to track their health conditions, manage the care of a baby, elderly or sick family member collaboratively, and share the care-giving responsibilities, even remotely. The platform allows the closest caregivers to be connected to the patient with visibility to the latest health conditions through updates on vital signs, manually or automatically via interface with vital sign sensors, in addition to the historical health conditions. Multiple alert levels can be configured remotely for different threshold conditions and caregiver groups. The platform uses various care scenarios including home healthcare, assisted living, nursing home or medical facilities. It also manages various state of health or types of diseases. The platform is an integrated solution to provide efficient, constant connections between the patients, their caregivers and the continuous monitoring of the health conditions. The environmental factors are monitored and adjusted automatically to maintain the best settings favorable for the patient's conditions. The platform advises the group members on the actions and choices for improving their health status, e.g., based on analysis of their health conditions, with support from the caregivers or other members in the group. Personalized advice and reminders, e.g., by close family members or friends is supported on this platform.

DETAILED DESCRIPTION

The software platform is based on a system architecture that is designed for: "distributed, hierarchical patient monitoring". Depending on the severity of the patients' conditions, some or all of the following three scenarios for care-giving may be applicable:

Patient self-monitoring (oneself)
Family/personal caregivers monitoring (M to 1)
Doctors/professional caregivers/nursing homes monitoring (M to N)

A mobile health platform allows members in the group to be connected and their health conditions to be monitored by each other, based on the pre-configured options. The design allows immediate family members, distant relatives, neighbors, friends and/or other caregivers to be included in the group.

The platform supports users with a desktop PC, smart mobile device, feature phone, or plain old telephones, with features adapted to their device capability.

Figure 13:
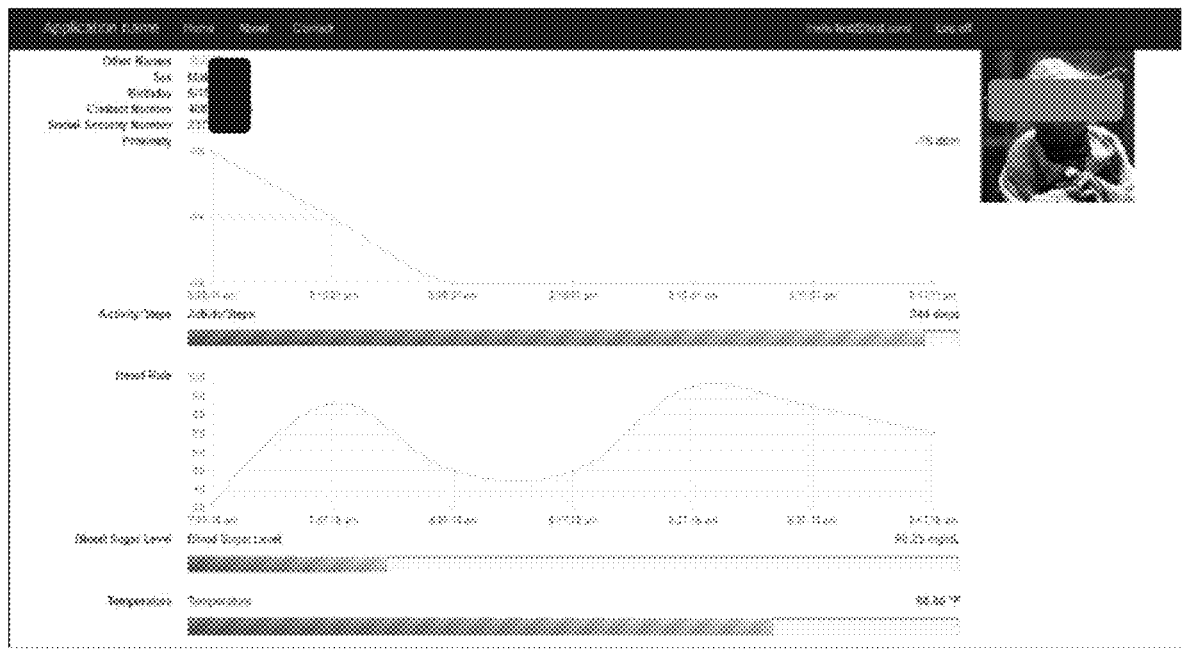
FIG. 13 shows an activity monitoring of a patient through a web application.
Figure 14:
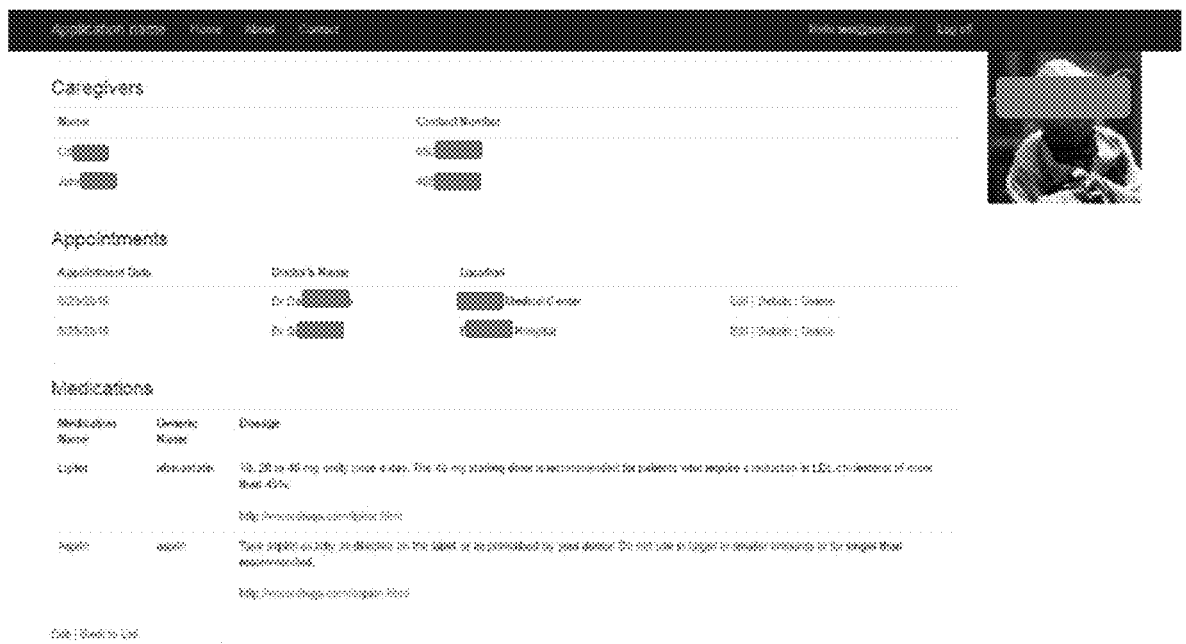
FIG. 14 shows the detailed patient data through a web application.
Figure 17:
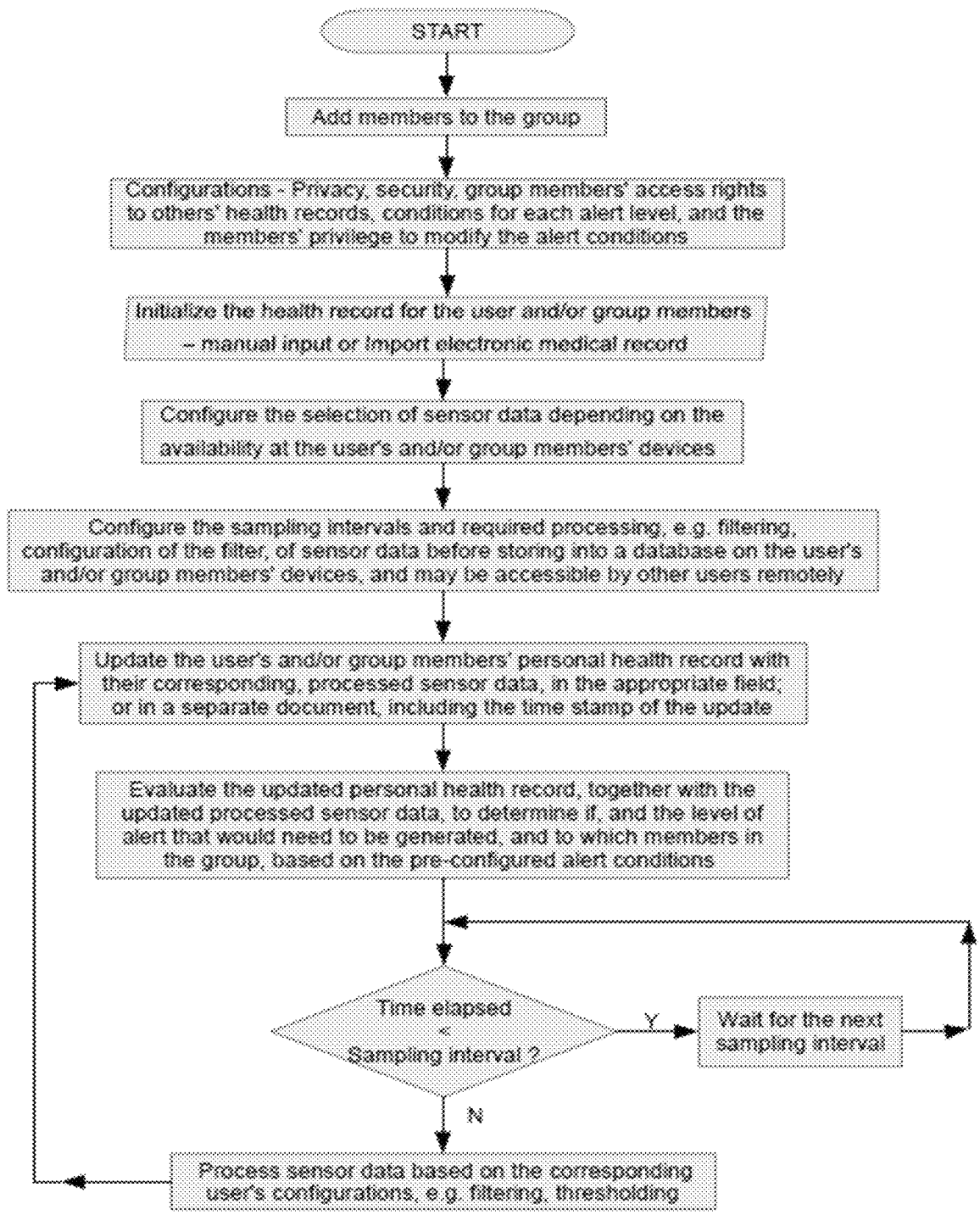
FIG. 17 shows a flow chart of the work flow of collaboration between patient and caregiver groups.

The software platform provides an efficient tool for a patient's health conditions to be monitored from anywhere communication and connectivity are available. The medical history of each member, including but not limited to: doctor's appointments, test results, diseases history, medication and allergies, recent vital sign measurement data can be stored and updated in the personal health record, by everyone in the group who has been authorized by the patient. FIG. 13 and FIG. 14 shows the detailed patient data. Besides, members in the group would be able to communicate with each other, e.g. with updates on the patients' health conditions, and coordinate any actions that need to be taken subsequently. FIG. 17 shows a flowchart for the workflow of how patient and caregiver groups collaborate with each other. The updates can be provided automatically, e.g. via a physiological sensor or biosensor with wireless connectivity, or entered manually, based on vital sign measurements taken manually, or patient's self-reports.

The distributed health monitoring system would enable simpler action and earlier intervention to be taken by the caregivers, minimizing the need to seek for professional medical help unnecessarily. This would improve the quality of life for the patients, and reduce the cost for all stakeholders. For patients who are cared by their dependable family members, neighbors, friends or nursing home caregivers, they would receive a faster response and attention from their personal, dedicated caregivers who would be the "first responders" using this solution.

The escalation of alerts to the professional care team involving the provider would be triggered only when the conditions are worse than those for the first trigger to the caregivers, or the intervention by the first responders are not effective in improving the patient's conditions. There will be different thresholds and conditions for comparison with the vital sign and sensor measurement updates to determine the triggers at different levels.

The system and protocol architecture are chosen with considerations on the privacy and security of the personal health and medical data, e.g. meeting HIPAA compliance, which would be stored with encryption in individual devices that are authorized by the Master user. The Master user can select to have the data backed up in the personal desktop computer, hard disk, server or a personal cloud service. This would ensure the users and/or patients to have full ownership and control of their own data that are collected by their own devices. The patient may proxy the privacy rights to a caregiver who can also be the Master user. The personal health records can be connected to the electronic medical records which are the official records typically owned by the medical service providers and updated after patients' visits with the medical professionals. In contrast, the personal health record would keep track of a patient's health conditions anytime. In the US, this can be done through the Fast Healthcare Interoperability Resources (FHIR) interface. Patient's medical information, e.g. vital signs, medication prescriptions, lab results, radiology results, procedures and other test results, can be retrieved through the FHIR API calls. Both records can be combined to analyze and compare the patient's conditions for thorough assessment.

Medical Knowledge

The solution would provide the patients and/or their family/personal caregivers with access to pre-screened information about various diseases, symptoms and treatment options. The increase of medical knowledge would empower the patients and their families to make better decisions on when and where to get professional help, based on their observations of the patient.

Use Cases

The solution supports a variety of scenarios for various types of caregivers and user/patient conditions. A few examples are described in the following subsections. The first one compares the various types of caregivers followed by the subsection which describes various users/patients with different diseases and conditions.

Support on Different Types of Caregivers

Family

Figure 1:
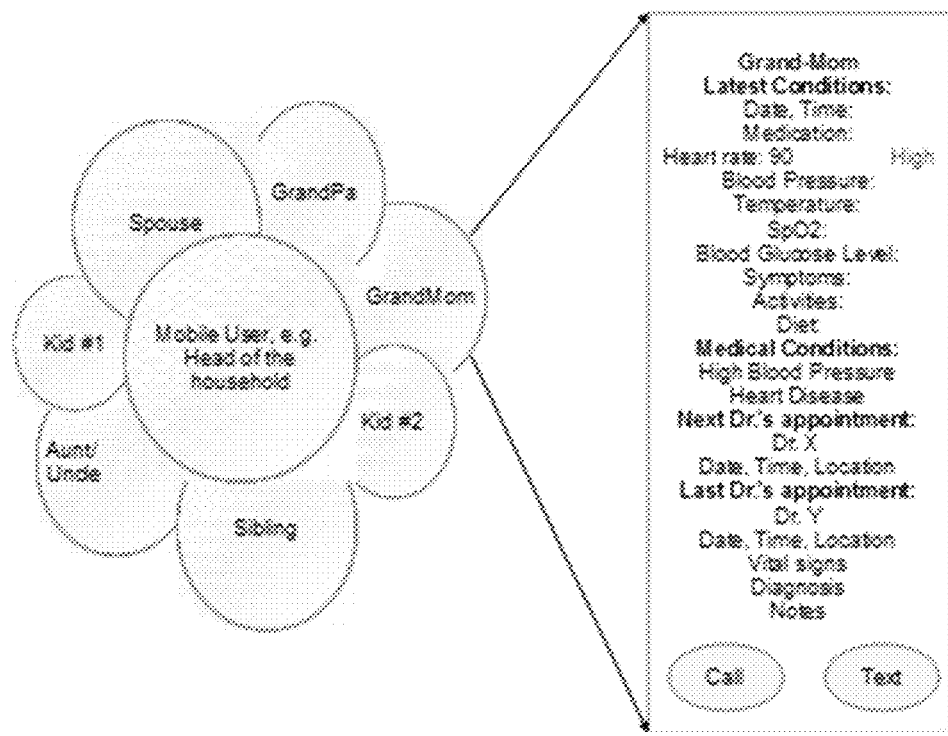
FIG. 1 shows an example of the User Interface showing the caregiving scenario between family members.

Members in a family are connected through the mHealth software system, such that they can access and exchange information, such as the medical conditions and health records via the platform as described in this document. FIG. 1 shows an example of the User Interface showing the caregiving scenario between family members. In such a "care" group, members are connected virtually. Members of a family can monitor the conditions of a sick family member remotely. Regardless of the communication device technology that is available to the patient, e.g. someone with only basic phones, their health information, including health records, doctor's appointments, medication can be managed by their family member's smart devices, with alerts configured periodically, or triggered by certain events happening to the patient.

Nursing Home

Figure 2:
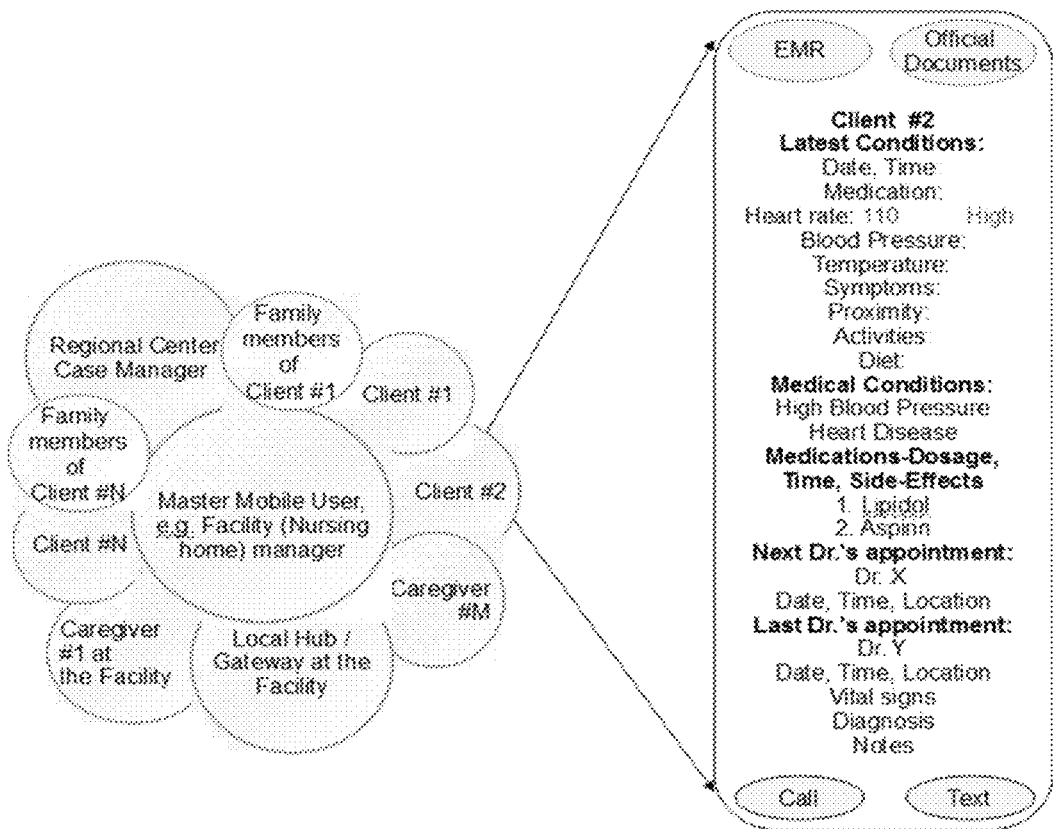
FIG. 2 shows an example of the User Interface showing nursing home caregiving scenario.

In the scenario of an elderly patient living in a nursing home, the nurses or staff there may use a desktop computer, laptop, tablet or smartphone to monitor multiple elderly residents simultaneously. FIG. 2 shows an example of the User Interface showing nursing home caregiving scenario. The nursing home staff should be able to check the elderly patient directly within a few minutes. The software provides an integrated solution so that new vital sign measurement data can be added to the patient's medical record on the mobile devices running the App.

The app would allow connections to the family members of the clients at the nursing home/care center facility, such that they can have access to the record of that particular client from their family. The case managers, e.g. from the regional center, are also connected to the manager of the care center facility, with access to their own clients' records, but not the others, as shown in FIG. 1 and FIG. 2 below. Besides the interface with electronic medical records, the app would also provide an interface to various official documents, e.g. power of attorney, advanced directives, treatment agreements that are accessible to both the elderly clients, their pre-authorized family/friends and the professional care team.

Professional Medical Care Team—Providers, Doctors and Nurses

Similar to the scenario of the nursing home, the professional care team can use the software system to monitor and manage the disease conditions of multiple patients simultaneously. When a patient's conditions have worsened sufficiently to trigger the second level of alert to the care team at the provider's side, the recent vital sign measurements and other conditions of the patient will be sent to the team together with the alert. The system provides the care team with the interface to contact the patient and/or caregivers via voice call or text messages. In addition, the system allows the care team to access the recent medical data collected for that patient remotely, and to modify or suggest the threshold configurations for alert triggering.

User Types

Various users as shown connected in FIG. 2 can be categorized into different groups based on the privilege levels and client device technology capability:

Privilege Levels

1) Administrator—The most privileged user category would have the right to add or remove users to the group. Users in this category can also determine the privilege level of each user in the group, e.g. access to certain document and information of any other individual user in the group.

2) Client/Family members of the Client—Default privilege only limited to the access of the client's own document, records and other information; Additional privilege to access additional information to be determined by the administrator, e.g. access to a client's info by other caregivers 3) Super Client—Higher privilege than normal clients who are residents at the care facility and their families; For example, this can the case manager of a regional center who has assigned one or more of their clients to this care facility; Can access all the records of their own clients.

Client Device Technology Capability:

1) No mobile devices—their medical/health records maintained by the other authorized users in the group, manually;

2) With mobile devices, no sensors—their medical/health records can be maintained by themselves and/or other authorized users in the group, manually;

3) With mobile devices, with sensors—their medical/health records can be maintained by themselves and/or other authorized users in the group, manually; some measurements and status updated automatically via the sensors;

4) With wearable sensors, no mobile devices (e.g. cell phones)—A hub/gateway at the facility communicates with the wearable sensors of these clients, updating their records with the measurement data directly;

5) Hub/Gateway—Connected to the group as one of the client nodes, with the difference that it can connect to the wearable sensor devices on those clients who do not have their own mobile devices to collect their own measurement data. For example, this can be a tablet computer running the mHealth app and/or maybe others that can communicate with the wearable devices on the clients User Scenarios for Various Disease Conditions The mobile application is used for monitoring and management of users or patients with various health status or disease conditions. It provides a platform with which the medical histories, the recent conditions and real-time measurement data for the patient can be organized and shared among various people who are involved in the caring of the patient. In addition to data sharing in a secured, private networking environment, the platform integrates the essential functions for people in the various caregivers' groups to communicate with each other in real-time so as to collaborate on the caring of the patient.

Wheelchair Users

The health status of the wheelchair users varies widely. The needs of those wheelchair users who are also patients with various disease conditions are described in the subsections below. A common need of the wheelchair users in the above categories would be the ability to get help from others when they are limited by the mobility, for example, when they need to evacuate from a dangerous situation, e.g. a fire, storm, tornado. The emergency alert system should be connected to their caregivers who are nearby. Besides, the software system will relay an emergency alert text message to the caregivers group that is connected to the wheelchair-bound user, whose location is tracked and shown to the group. Suggestions on escape routes can be provided by the software system, based on the location of the user and the correct information on the hazardous locations. A caregiver who is nearby would be able to help the wheelchair user to evacuate from the location. If a caregiver is not nearby the user, a "Please help XX on a wheelchair at YY location" message can be broadcast to users of the similar app in the immediate neighborhood of the user.

Users with High Blood Pressure

For users with high blood pressure conditions, it would be helpful to monitor their blood pressure regularly. The patients who are diagnosed with such conditions would be prescribed medications to control their blood pressure. It is necessary to ensure the medication is being taken as prescribed to avoid further deteriorating conditions from happening.

Ideally, a patient with high-blood pressure should monitor their blood pressure variations throughout the day, such that interventions such as medication can be taken when the blood pressure is near it highest level, e.g. within $x=70\text{-}80\%$ of the highest recorded blood pressure previously. Depending on the time required for the medication to take effect, and how fast the blood pressure is increasing, the percentage x can be calculated by the software system. It would also take into considerations the previous dosage and time at which the medication was taken.

When such a condition of high blood pressure is detected, e.g. through continuous or regular blood pressure measurements, the mHealth mobile Application will alert the patient and the caregivers in the group about the need for medication. The alert will stay until the patient has taken the medication and responded accordingly to clear the alert. The blood pressure measurements would be recorded at shorter intervals to detect the changes in the blood pressure levels. The data would be used to estimate the response time to the medication, i.e. duration from the time the medication is taken to the observation of a significant drop in blood pressure, and the rate at which it decreases etc.

The monitoring and measurement of blood pressure levels can be obtained by sensors or measurement systems attached to the patient. The measurement data should be recorded on the mHealth App at regular intervals, manually or automatically, depending on the type of system available to the user.

The recorded blood pressure measurement data throughout the day, before and after medication, are stored on the mobile device or backup in the desktop computer, storage device or a private, secured network storage location. They can be pre-configured for access or shared with the provider's, i.e. the nurses and doctors in the care team, before the follow-up appointment, or immediately, in case of an emergency situation.

Cardiovascular Disease

Figure 3:
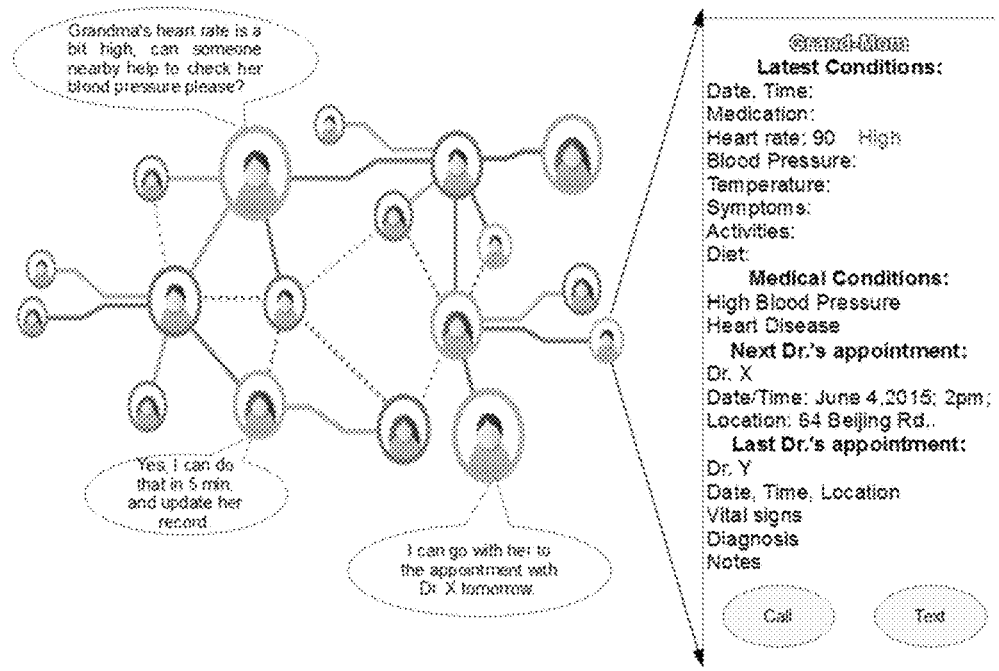
FIG. 3 shows an example showing an elderly's medical conditions, records, medication adherence and appointment information—managed collaboratively by the caregivers in the family.

Using the mHealth platform, family members may help the elderly parents or relatives to monitor their heart disease conditions. FIG. 3 shows an example showing an elderly's medical conditions, records, medication adherence and appointment information—managed collaboratively by the caregivers in the family. For example, medication adherence can be tracked using the mHealth platform, together with the record of heart rate, blood pressure and/or ECG measurements. Follow-up appointments scheduling will be part of the records for the elderly patient, with reminders sent to members of the family, for their coordination of care-giving responsibilities.

The measurements of heart rate, blood pressure, temperature and/or ECG etc. can be collected either manually or automatically through the use of mobile medical devices like physiological sensors. Depending on the accessibility and accuracy of the wearable sensors, additional vital signs may be collected by the mHealth platform directly.

The mHealth platform will include a way for an alert to be sent to the family, e.g. based on the early detection of an emergency. This can be done by analyzing the most recent measurement data samples to determine if there is any abnormal change in the "trend" of the changes in vital signs, as compared to the normal conditions of the patient, to determine if an alert will need to be generated.

Users with GI Issues

A user with GI diseases may share the symptoms and discomfort status using the mobile device platform. The caregivers or family members who are connected in the group could provide suggestions on what the patient could do to try to relieve the symptoms. In case the symptoms persist, the patient would need to consult with a medical profession, e.g. through a Telemedicine application or visit a clinic.

The most basic solution would be based on self-reporting of symptoms, e.g. stomach ache, acid reflux, or diarrhea recording the time when they happened, noting the time and types of food and drinks taken prior to the onset of symptoms, e.g. by scanning the food packaging or taking a picture of the food. Over the counter medication such as Prilosec may be used with the time recorded, noting if the symptoms were fading away. Based on the type of medication, the App can alert the patient at the time when the medication can be taken again, e.g. at intervals of four or more hours. The patient may enter their state of the symptoms, e.g. improvements by "N" levels, for N=1-10, where N=10 means that the symptoms have disappeared, and whether the medication is taken at that time. The tracking can be recorded using a similar format as shown for the pain management in FIG. 16.

A few different types of sensors for detecting GI issues have been developed. The classic approach is to measure the PH level inside the GI tract, e.g. stomach. Another non-invasive approach has been developed using external sensors that detect the movements in the GI tract, based on the application of signal processing techniques to the measurement data collected by the sensor array. When those sensor technologies are approved by the regulatory bodies and become available commercially, the GI issues may be predicted with warning provided in advance through early detection. The effectiveness of the medication may be determined through the changes in the measurement data collected by the sensors, before and after medication is taken.

Another way that this App can help users with GI issues is to send them regular alerts at the time for medication, and regular meals or snacks, with suggestions on the type of food to eat or avoid, based on the GI history. The alerts at time interval between meals and diet can be configured and adjusted during the doctor's appointment, remotely by the doctor, nurse, dietitian or by the caregivers per doctor's instructions. For example, when the patient has a stomach ache, the medication has to be taken as soon as possible, followed by a light meal with easily digestible food that can help to balance the PH level inside the stomach. As the patient's conditions improve, the variety of food can be increased slowly without overloading the stomach.

The alerts can be a simple pop-up on the user's device with a reminder for meals, or it can display photos and links to nearby restaurants, cafes or grocery stores which have menu items suitable for the user's diet. To reduce interruptions to the users, the alerts for meals can be combined with those for the other events on the user's calendar, within a similar time frame, e.g. 15 minutes.

Using this App, the diet requirements for the patient are shared among the other members in the group, e.g. the cook for the family would be aware of the diet requirements when the meal is prepared.

Patients with Respiratory Problems, e.g. Asthma, COPD or Lung Cancer Patients

For patients with respiratory diseases, their blood oxygen concentration level would be lower than normal people, while the carbon dioxide level is usually higher than normal. A patient with such diseases should have their blood oxygen concentration level or carbon dioxide level measured and monitored continuously. The measured data by the sensor can be transmitted wirelessly to the patient's mobile device, an access point (hub) and/or a computer. Besides, other vital signs, e.g. the heart rate and temperature of the patient would also be measured and monitored by the same or a separate sensor that will also transmit the measurement data to a mobile device, an access point and/or a computer.

The mobile device or computer would process the measurement data received from the sensors, e.g. by filtering the noise using a moving average filter, over a configurable duration, e.g. per second/minute etc., depending on the resolution required and the patients' conditions. The filtered measurement data are then compared with a configurable threshold to determine if the patient's condition has worsened.

If the filtered measurement data, e.g. blood oxygen concentration level, heart rate, falls below the first threshold, a level-1 alert will be generated to inform the caregivers who are the closest to the patient. In case of heart rate, carbon dioxide level, an adverse condition would be triggered when the measurements are above their respective thresholds.

As an alternative configuration, the measurement data need not be filtered at the mobile device or computer. They may be transmitted by the sensors at the desirable, configurable intervals, e.g. per second/minute etc. In some configurations, the sensor modules would have included some filtering and signal conditioning functions.

The App will also collect environmental sensor measurement data, e.g. temperature, humidity and air quality etc., besides the vital sign. The environmental information can be collected from a smart thermostat or smart air purifier/air quality sensor which can send the measurement data via wireless connection to the mobile devices. The patient or caregivers would be alerted when the environmental conditions may cause a flare-up of the patient's condition.

A closed-loop control mechanism can be used to adjust the fan speed/air flow at the air purifier or the temperature setting at the thermostat, when the environmental conditions may have caused worsening of the patients' vital signs. It may also be used to adjust the oxygen flow rate at the oxygen tank or concentrator, through commands sent via the wireless link connecting a mobile device to the instrument.

Diabetes

For Diabetics patients, the blood glucose level would need to be monitored regularly. Traditionally, this is done by punching the finger tip of the patient to get a drop of blood onto a test stripe which is then inserted into a meter to determine the blood glucose level. Using this app, the measured blood glucose level can be entered into the record sheet in the mobile device. This helps the patients and their caregivers to keep track of the changes in blood glucose levels, at different times of the day when the test of taken. The app will automatically associate the recorded level with the time and date at which the data was entered. Alternatively, the measurement data can be entered into the patient's record automatically through a connection interface between the device that reads the blood glucose levels and the mobile device.

Moreover, continuous monitoring of glucose level would be more beneficial for the patients. This could be done by analysis of the patient's blood, tears, saliva or sweat using appropriate sensors. With bluetooth or other wireless modem integrated into the sensor modules, the real-time measurement data can be transmitted to a mobile device which is running the app, such that the patient's record would be automatically updated with the latest measurement data.

An insulin pump that has a wireless interface can enable the remote adjustment of the amount of insulin in accordance with the blood glucose level. The flow of insulin at the pump can be adjusted through a closed-loop control system, based on the measured blood glucose level, such that a desirable level can be maintained.

The mobile platform can be used to adjust the flow control of the insulin pump wirelessly. The app would calculate and adjust the dosage of insulin necessary to maintain the desirable blood glucose level, through continuous monitoring of the blood glucose level, taking into account the response time required for each insulin injection. The response time can be estimated based on historical data, e.g. through the monitoring of blood glucose level changes, at shorter time intervals, starting at the time a certain dosage of insulin is injected.

The blood glucose level sensor can be integrated with the needle for the insulin pump, such that there is no need for a separate needle for blood glucose sensing.

Pre-Diabetic Users

The pre-diabetic users are those who are likely to develop diabetes in a later stage in their lives, based on their fitness level and life styles, e.g. low activity levels and high sugar, high fat diets. Most of those with high BMI values and/or with obesity are very likely to becomes diabetics, soon or later.

It would be worthwhile for the App to help users with these conditions to avoid from developing diabetes. The solution supported by this App would provide suggestions, plans and tools for these users to improve their health status, e.g.: Choice of weight loss programs—Nutritional diet with different variations, e.g. Meals with different ratios of meat to vegetables, all of which should be less than 0.5; Exercises; provide links to resources on training classes, coaches, MeetUps for various sports activities.

The App provides a connection between the pre-diabetic user to the family or close friends. The family and friends who are connected via the App can remind and encourage the pre-diabetic user, e.g. when exercise would be needed, and/or when meals are prepared for the pre-diabetics.

The motion sensors carried by the pre-diabetic user, e.g. in the cell phone, smart watch or wearable devices, would provide information on the amount of activity on the App that is shared by users connected in the group. The selected diet plan can be read by those in the user's group who would then help the user on the weight loss program, by providing reminders and suggestions for dinners etc.

Patients with Emotional Issues, e.g. Depression, PTSD etc.

The platform can help these patients through their "always-on" connections to their family, friends, such that any changes to their activities and responses can be used for symptom detection, i.e. at the onset of depressive mood. For example, there can be a message pop-up asking if they are happy at a certain time. If the answer is: "No", or no response, an intervention can be triggered automatically or through their connection in the App, as they can see the response immediately.

The supportive connection can then provide some ways of alleviation, e.g. phone call to chat, or sharing of music to help with relieving the symptoms.

Parkinson Disease Patients

Through the detection of shaking, instabilities, jittering, it may be possible to avoid the patient from falling, e.g. through the use of a fall-prediction algorithm. Thus, before the predicted time of a fall, the caregivers nearby can be ready to support the patient from falling. With the constant connection with caregivers, e.g. family members or neighbors would be alerted of a fall or the prediction, so that they can respond promptly to help the patient.

Alzheimer Disease/Dementia Patients

Figure 12:
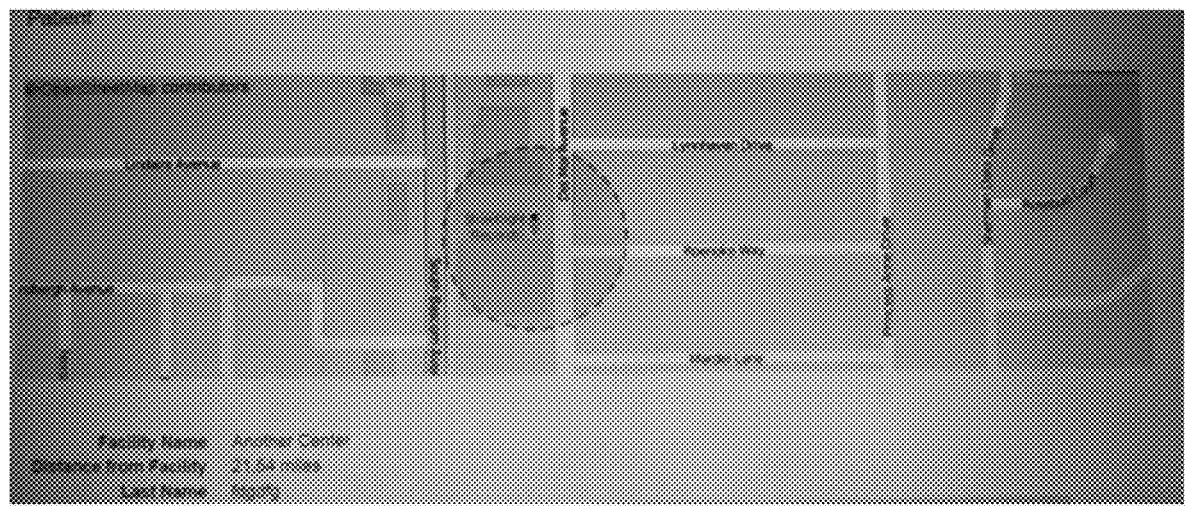
FIG. 12 shows an approximate location of client (with Bluetooth Device): blue circle centred around the care home—Alerts care home staff when the client wanders too far.

The location of the user, which is available in all mobile phones via GPS, or a combination of GPS, wireless and/or cellular network user positioning mechanisms, or a special GPS location tag that is carried by the user, e.g. an Alzheimer patient, can be shown to the connected group members to locate the patient who may have lost his/her way. FIG. 12 shows an approximate location of client (with Bluetooth Device): blue circle centred around the care home—Alerts care home staff when the client wanders too far.

As an alternative to a device with GPS receiver and cellular communications capabilities, the distance of a simpler wearable device from a host device can be used to detect the distance of the user from the host device, via the wireless connections. For example, as the wireless signal strength is a function of the distance between the transmitter and receiver, it can be used as an estimate of the distance, with some calibrations.

In one scenario, the dementia patient may have a tag with Bluetooth connectivity, which connects it to a hub/gateway located inside the nursing home where the patient resides. A tablet computer can be used as the hub/gateway in which one or more Apps are running. If the patient wanders outside the house, e.g. for a distance more than X meters from the hub, then an alert would be generated by the App. There will be notifications sent to the other caregivers/mobile users who are connected to the App. The value of X can be determined depending on the distance of the hub from the exits of the house, such that the alerts can be triggered as soon as the patient stepped out of the door.

The tag to be carried by the patient can be in various form factor, e.g. necklace, bracelet, ring, hairpin, earrings, attached to the clothing or shoes. It can be a commercial product, or a custom-made device with Bluetooth or other wireless connectivity. The App running at the hub will estimate the distance of the tag based on the strength of the received wireless signal that was transmitted from the tag. In case that information may not be accessible in a commercial off-the-shelf tag, then the App would need to make API calls to retrieve the distance info of the tag and the patient.

In the case of a custom made device, it would consist of a wireless modem, e.g. Bluetooth transceiver, an antenna, a power supply or as an alternative: a solar cell, pressure sensor, piezo-electric device or other energy harvesting circuits, in its simplest form, to transmit and receive signals from the hub.

Infants and Children

Figures 15, 16:
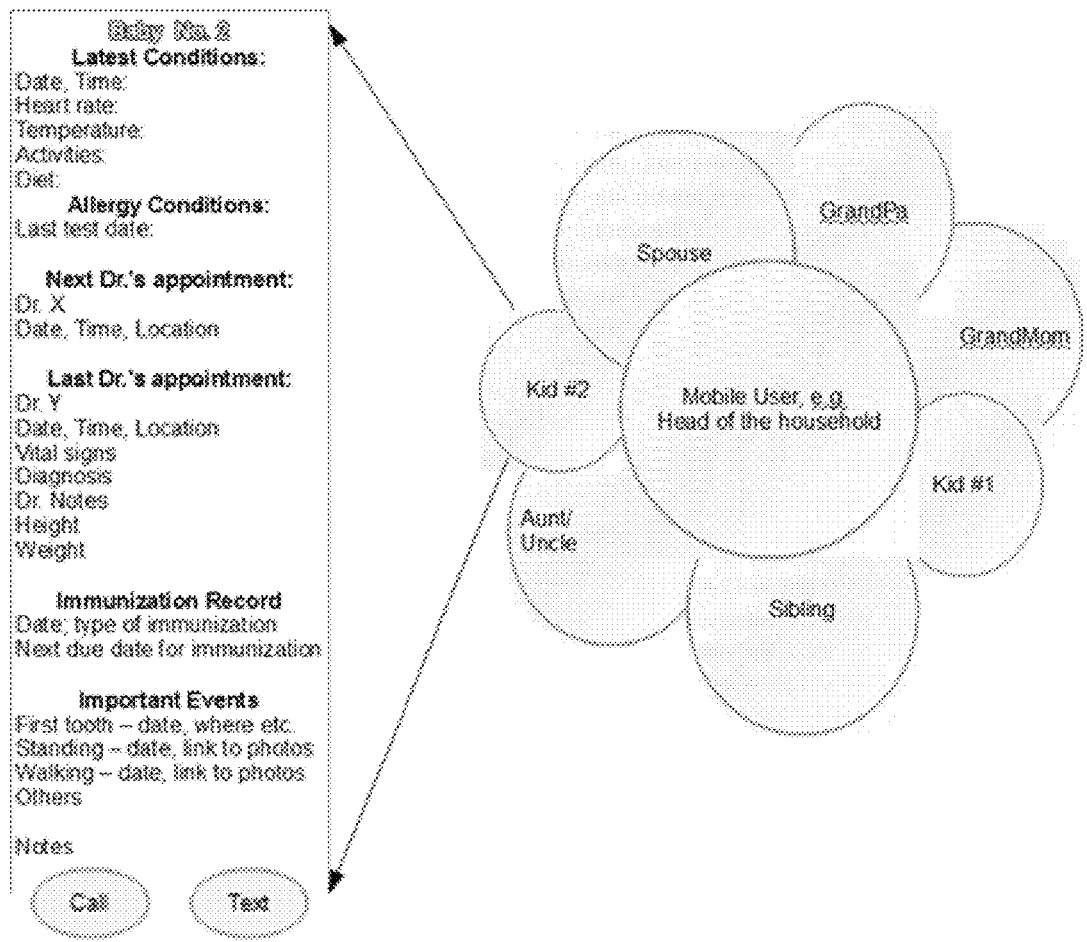
FIG. 15 shows the user scenario for managing the healthy growth of a baby.
FIG. 16 shows a table for pain tracking.

The app can be used to start organizing and storing an infant's growth and medical record, e.g. Regular temperature measurements; Regular height, weight measurements; Immunization record; Diet: meal—type, amount etc.; Days of special events: first tooth, first time to stand and/or walk, first word spoken; Pointers to the events would be available to help the users to retrieve the photo or video. FIG. 15 shows the user scenario for managing the healthy growth of a baby. This would document the infant's personal health record, from the very beginning. Location of children who do not yet carry a cell phone can be determined by other ways, e.g. using wearable devices with location tracking capabilities, RFID tags etc., similar to that used by a dementia patient as described above.

Healthy Users

As it has been recommended by the World Health Organization, the US Surgeon General and the American Heart Association, an adult should perform a minimum of 150 minutes of moderate exercise per week, to prevent against various chronic diseases. Healthy eating habits have been recommended for chronic disease prevention, e.g. through myPlate or the Harvard food plate. Besides, adequate sleep time with good quality is also important to one's health.

Thus the App would provide information to help the healthy users to maintain their healthy status. Similar to the monitoring of patients with medical issues, the App would gather information from the wearable devices, e.g. activities level and duration, sleep duration, heart rate etc. By analyzing the data and display the results in an intuitive approach, the users can learn and get advice on whether they need to increase their activity levels and improve their sleep. Below is a list of additional features to support healthy lifestyle choices and habits, for example:

Suggestions on nearby restaurants with healthy menu items, with nutritional information, including the health benefits associated with the ingredients, e.g. broccoli, tomatoes with high anti-oxidants for cancer prevention; based on the user location as determined by the mobile device; Suggestions on opportunities for exercises, e.g. walking, hiking trails, swimming pool and sports courts nearby; information can be provided when the user searches for directions to a certain location to remind the user to plan the exercise time as part of the trip; based on the user location as determined by the mobile device; Ad hoc meetups for people who are located nearby, e.g. as posted on Meetup.com, Eventbrite or, events happening in the time frame when you travel to a neighborhood; Connections with family members, friends or neighbors would facilitate the organizing of physical activities jointly, which would help to motivate and sustain the habit of exercise; Activities can be tracked automatically to estimate the level of physical activities accomplished and suggest additional ones to meet the goal, e.g. joining other friends for a walk; Reminders are provided to the mobile device users to alert them the time for exercises; these can be configured as text messages, the user's favorable music, machine voice, or pre-recorded sound, pet's or human voice.

For example, a loved one may have pre-recorded a warm and gentle reminder, e.g. "Hey Friend, it seems that you have not done enough exercise today, would you like to go for a walk before the sunset, which is forecast for an hour from now? Maybe you can try to return the missed calls as you walk." In this example, the pre-recorded message will be played at about an hour before the sunset, based on the weather forecast. Alternatively, this can be displayed as a text message at the similar time. The reminders for exercise can be set to a lower priority, and delayed until another higher priority event on the calendar has ended; Incentives can be provided to the user as encouragement when some significant improvements have been made, e.g. increase levels of physical activities as compared to the previous day, or the achievement of predetermined goals; Incentives can be in the form of a free music download which is beneficial for emotional health, coupons for Yoga, Zumba, or Taichi classes, free passes to the gym, or health food/drinks etc.; Incentives can be sponsored by various vendors which could make use of this opportunity for acquiring new customers or future sales; Weight information can be captured in a record for the users, e.g. manually or via wireless connectivity at the scale, if available.

Sleep Apnea

The App can be used to detect symptoms of sleep apnea and alert the users and/or their family or roommates to wake them up.

The user would have to wear a pulse oximeter (SpO2) sensor when they go to sleep, ideally wearing an activity tracker at the same time. The App would monitor the SpO2 level and heart rate while the user is sleeping. When a drop in the SpO2 level is detected below an abnormal level, it serves an indication that there might be an obstruction in the user's airway. An alert would then be generated to wake up the user, caregiver or roommate to make sure the user change the position of sleep to allow clearance in the airway.

Chronic Pain Management

Tracking of pain symptoms, location, activities type, duration can be supported by the App, either manual or semi-automaticy, e.g. when a smart activities tracking device is worn by the patient. The information tracked would include the activity and its start and end time, the time when the pain was felt and disappeared, as shown. in the example in FIG. 16. Based on the information about the pain "profile", the App can estimate the approximate duration that the patient can engage in a certain activity and alert the patient to stop that activity and take a rest, before the pain hits. The t can be configured as the patient's favorable music, machine voice, or pre-recorded sound, pet's or human voice. For example, a loved. one may have recorded a warn and gentle reminder, e.g. "Hey Mom, it seems that you have been walking for a while now, would you like to sit down and rest a little bit, check your email or play an online game? You can text or call me to at if you like."

Features

1. Personal electronic health/medical record
    a) A personal copy of health/medical record can be created by and maintained by everyone using this platform.
    b) Collaborative review and update of the personal health record can be done by the caregivers and other authorized individuals.
    c) Integration with electronic medical record
2. Messaging—Users connected in the group can communicate with each other using text messages, voice and/or video messages. The voice or video messages can be configured to play back at specific times, e.g. at the time of medication, as a reminder to the patient. a) text; b) voice; c) Video
3. Calls—from simple checking/interviewing of the patient to remote consultation with an expert medical specialist in the field: a) Audio call: 1-1; b) Audio conference calls: >2 people on the call; c) Video calls: 1-1 or conference call. Members in the group may join a conference call consultation between the patient and a provider or professional care team to discuss the health issues and treatment plans. The personal health record with the latest measurement data and conditions collected through the continuous monitoring system can be shared with the provider or professional care team during the video call consultation. This system would improve the quality and experience of remote medical consultation or telehealth, through the provision of patients' recent and detail health information.

4. Measurements and record updating—a) Manuel; b) Automatic; c) Periodic; d) Remote trigger; e) Remote configuration changes.

5. Alerts—Different levels of alerts can be generated based on severity levels of the situations:
   a) Emergencies—Call the paramedics;
   b) Level 3—Notify doctor or medical professional care team for the earliest appointment or remote consultation using telemedicine;
   c) Level 2—Caregiver team, e.g. family or nursing home care, personal attention;
   d) Level 1—Additional measurements;
   e) Reminders.

For example, if the SpO2 level has started to drop below a certain threshold, when the activity level is unusually high, the App will generate a Level 1 or 2 alert to advise the COPD patient and the caregivers that the activity level should be reduced. At the same time, the App will continue to monitor the conditions of the patient more closely, i.e. sampling the SpO2 level, heart rate and activity levels, and check the environmental factors, e.g. temperature, humidity and air quality, more frequently. If the environmental factors have improved, activity level has reduced, but the SpO2 level or heart rate haven't improved, and the medication has already been taken, the next level of alert will be generated to notify the medical professional care team, which would be provided with access to the recent measurement data on vital signs, environmental data, activity and medication history for the past few hours.

6. Medication Information and Tracking
   a) Medication history—Prescribed, amount taken, effectiveness, side-effects;
   b) Current medication—Prescribed, amount taken, remaining quantity, effectiveness & side-effects;
   c) Information on medication—Expected responses (time), side-effects 7. Doctors' (Dr.) information—
   a) Upcoming Dr. appointments and past visits
   b) Other doctors nearby: education, experience, reviews
   c) Best doctors recommendations (ratings) References—identify in the network, e.g. through collaboration with other websites, or based on accumulated ratings by users of this App 8. Medical facilities information
   a) List of various facilities nearby, and at various distances: specialty & ratings
   b) Alternative medicine, e.g. Chinese medicine, Acupuncture, other holistic care
   c) References—identify in the network, with information verified before sharing it with the users 9. Provides information on emergency procedures, e.g. first aid, choking etc.

10. Nutrition, exercise and other advice.

System Architecture

A distributed, secured system architecture with flexibility in the number and configuration of end nodes can be implemented. In one option, there will be a Master user with the highest level of privileges to configure the privacy settings to allow different levels of access to different data files for various users connected to the group. In another option, each user can configure the privacy setting for sharing information with various users, if the user is the original owner of the data. There can be sub-groups within the group, such that some information sharing can be limited to the subgroup members, to ensure privacy under different levels of sharing. The software system may consist of one part that would run on various mobile devices that are connected through to the same group, and another part that would run on a remote server. It would be possible for the devices running the software to connect and communicate with each other, even without connection to the server or Internet. When Internet is available, and that it is desirable to connect to the server, the user can configure the devices to have the data backed up to the server, and/or perform certain computational operations. For example, the data backed up can be configured to perform during charging and/or under WiFi connection. This would imply that part of the database to be available on the users' devices locally, e.g. with the most recent and important information about the users.

Remote Patient Monitoring—COPD

The system design as described in the following sections is used for monitoring patients' conditions continuously, and to respond with various actions to improve the patient's condition, depending on the conditions and effectiveness of other actions, either manually, semi-automatically or automatically. Different components of the system are connected wirelessly in the patient's vicinity and remotely to the patient's care team, to allow remote monitoring and intervention, if necessary. A patient is equipped with various sensors which can be one or more integrated modules with wireless connectivity, e.g. to measure and track the patient's vital signs and activities continuously. Similarly, there may be other sensors in the patients' environment that can provide information on the environmental factors, e.g. temperature, humidity and air quality etc., through a wireless connection. In addition, there could be equipment and appliances that can be connected to the host device which may then control the settings and configurations of the former to improve the patient's conditions. The host device can be configured to alert the patients' caregivers and/or care team when certain conditions are detected which are not improvable through adjustments of the environmental conditions and equipment settings.

In general, some basic processing of the sensor data samples are performed by the microprocessor (MCU/CPU) at the sensor module before transmitting to the host devices. Some sensor modules may allow the software on the host devices to access the received sensor data, e.g. by decoding the data received via the wireless link with the sensor module. Other sensor modules may require a host device to transport the received data to a remote server without allowing the decoding of the sensor data at the host device. In the latter, the host device could issue an API call to the server to retrieve the sensor data after transporting them to the server.

Operation Scenarios

Indoor Scenario

When the patient is located indoors, the system can connect various types of sensors to a smart watch, smartphone, tablet and/or other computing devices, e.g.: Physiological sensors and/or Biosensors, e.g., sensors for heart rate, respiratory rate, blood oxygen concentration, blood glucose levels, temperature and activity level; Environment sensors on the home appliances, e.g., thermostat, air quality sensor at the air purifier, (de-)humidifier etc. Other sensors on the mobile device or other wearables that the patient is carrying, e.g., motion sensor, accelerometer, gyroscope etc. sensors on medical equipment, e.g., oxygen concentrator, or oxygen tank, or insulin pump.

Figure 4:
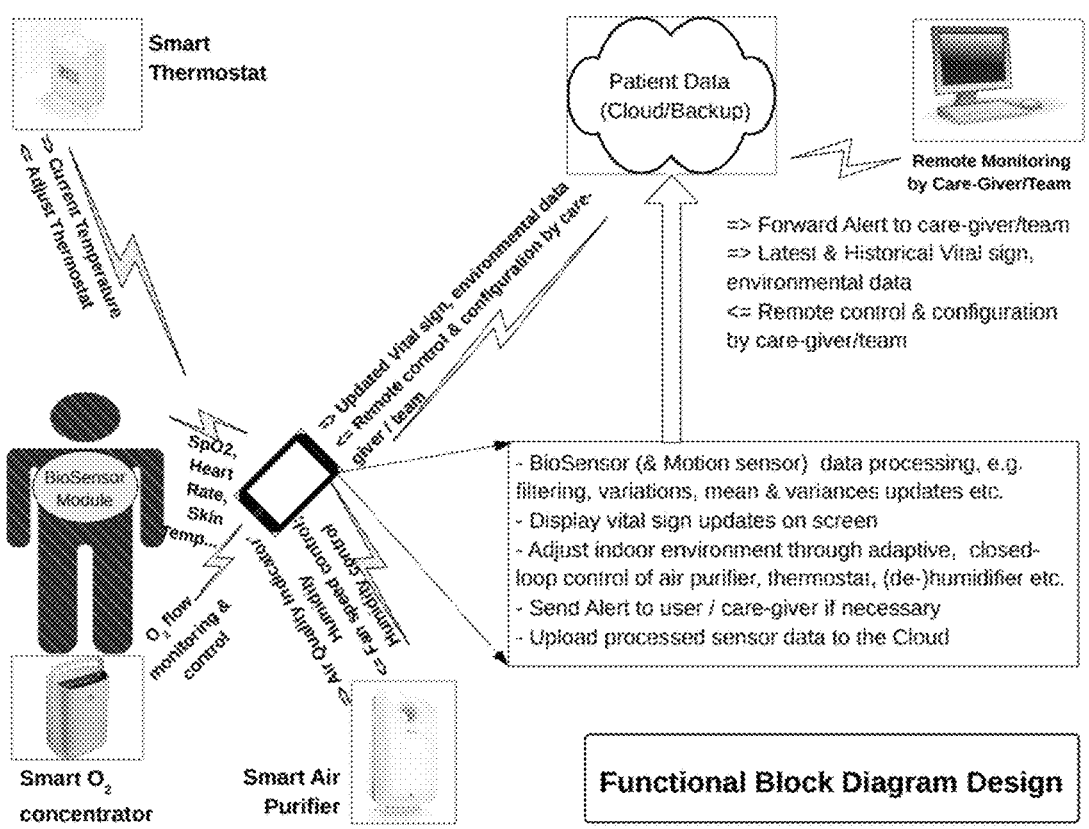
FIG. 4 shows a Functional Design Block Diagram—Direct access to sensor data.
Figure 5:
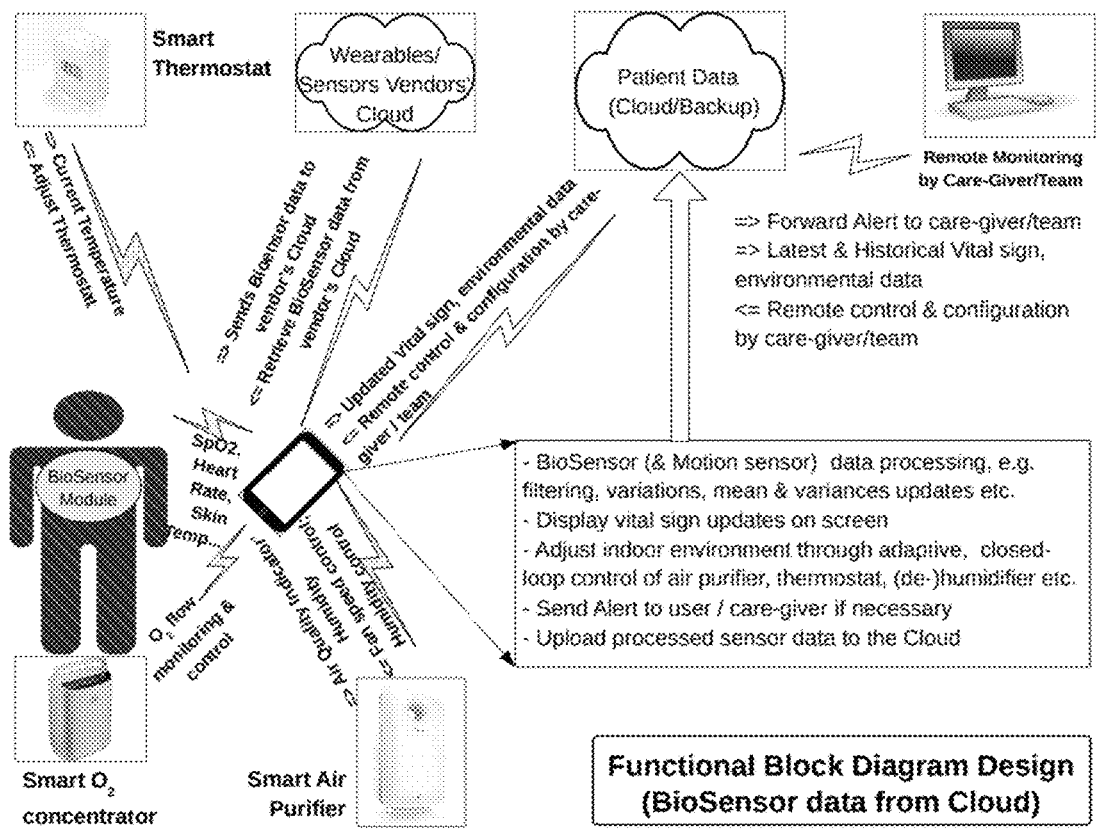
FIG. 5 shows a Functional Design Block Diagram—Access to Sensor Data via Vendor's Cloud.
Figure 6:
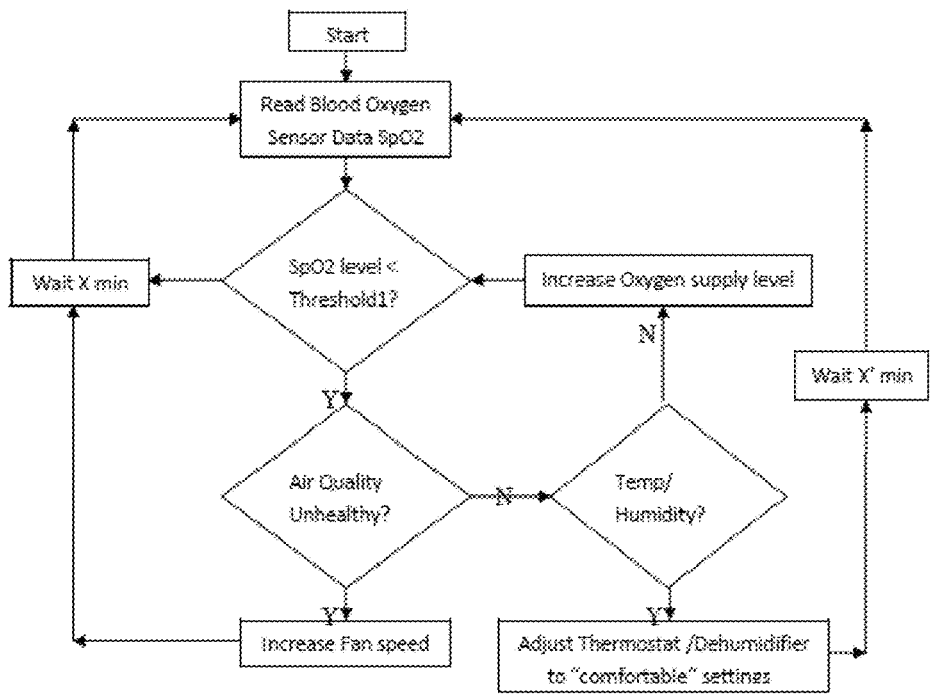
FIG. 6 shows a flow chart diagram for Automatic Environmental Control for COPD Patient Management.
Figure 7:
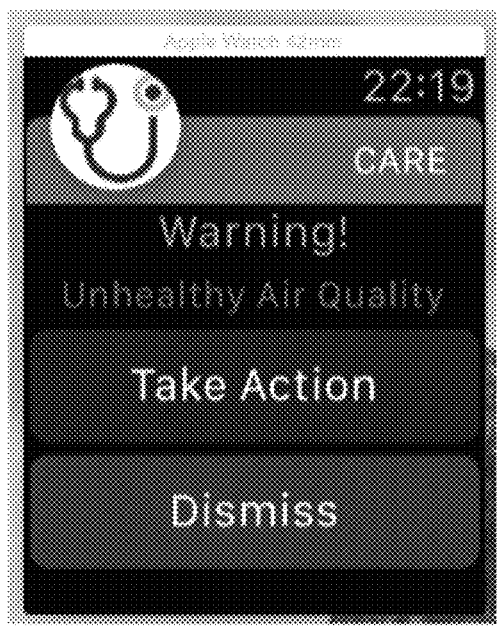
FIG. 7 shows an example of an Alert on Unhealthy Air Quality.
Figure 8:
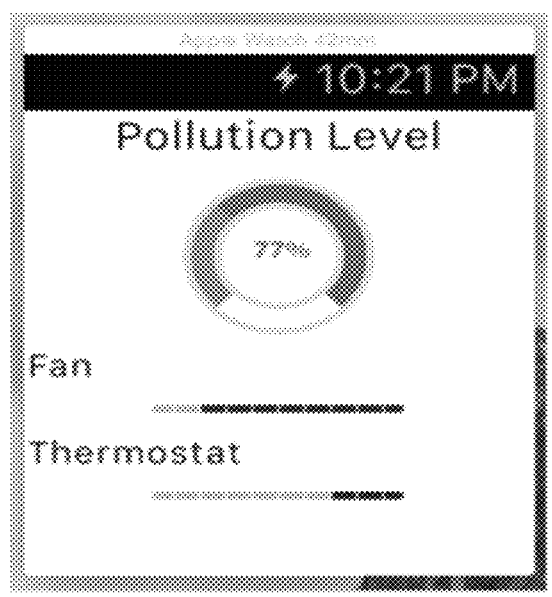
FIG. 8 shows an example of Remote Adjustment of Smart Air Purifier Fan Speed and Thermostat.
Figure 9:
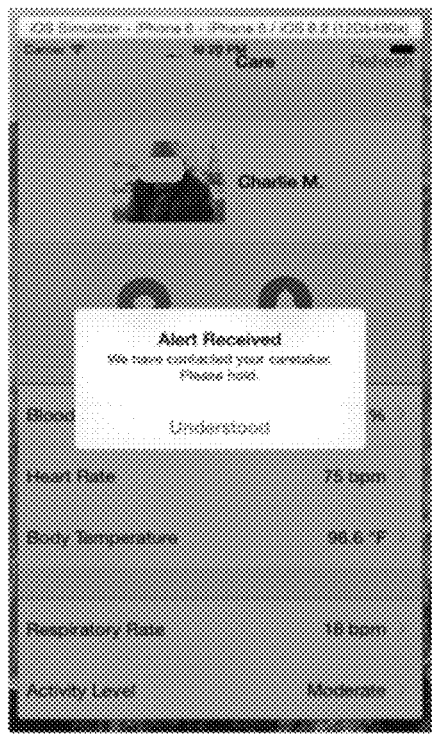
FIG. 9 shows an example of an Alert Sent from the Patient's Smartphone to the Caregivers and/or Care Team
Figure 10:
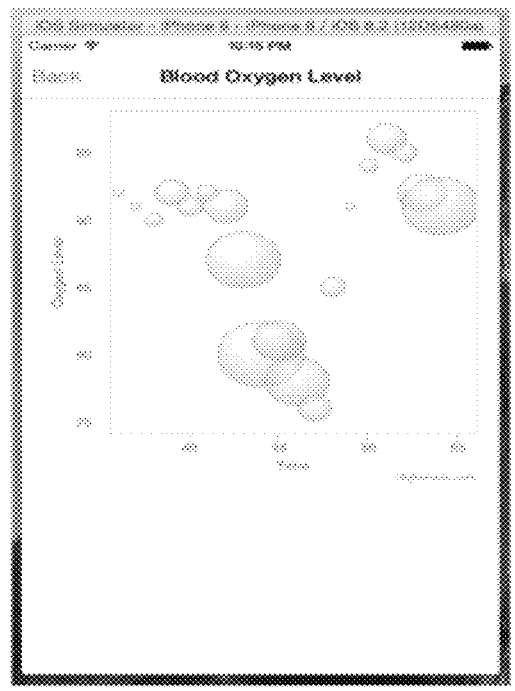
FIG. 10 shows a Graphical Display of the Variations in Patient's SpO2 and Activity Levels.
Figure 11:
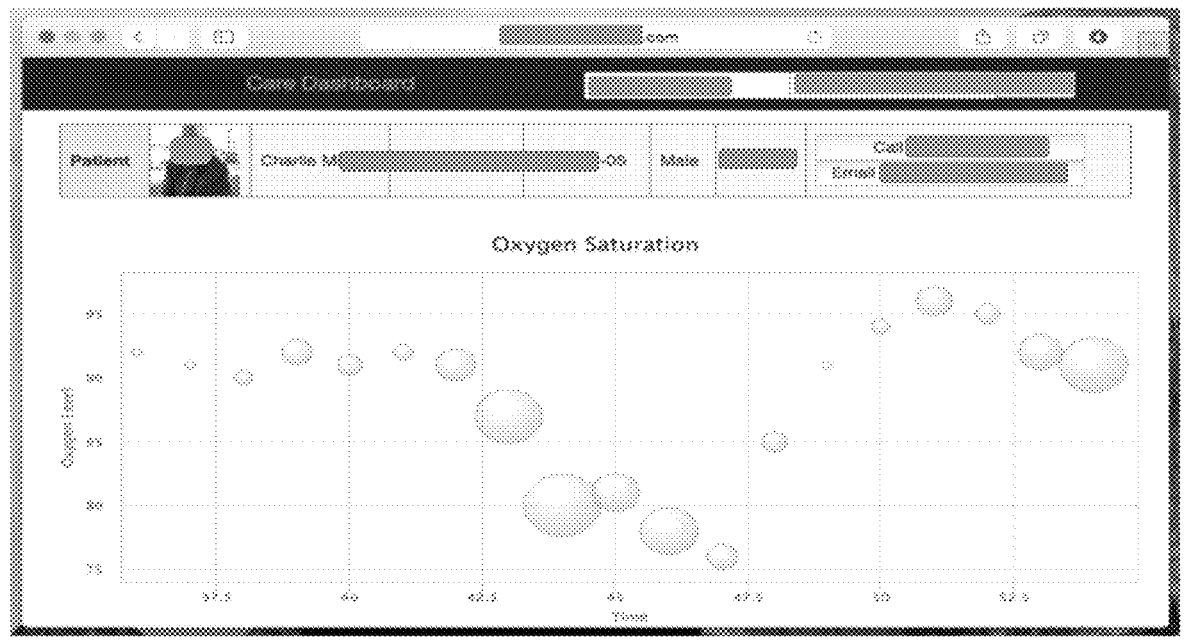
FIG. 11 shows an example of a Plot of the Time Variations in the Patient's SpO2 and Activity Levels at the DashBoard App for the CareGivers and CareTeam (Remote).

On a regular basis, the physiological sensor data is received by the patient's App, which can be run on a smart watch, smartphone, tablet and/or other computing devices. The sensor data is processed, e.g., filtered, de-noised, averaged, and compared with some thresholds to determine the patient's condition and respond in correspondence, as shown in the block diagrams FIG. 4 and FIG. 5. In the manual mode, the patient is alerted of "Unhealthy Air Quality", e.g. per the air quality indicator as received from the smart air purifier, with an user interface that allows the change (increase in the case of unhealthy air quality) of fan speed at the smart air purifier, and adjustment of the thermostat, as shown in FIG. 7 and FIG. 8. When the patient's condition is worsened, an alert can be sent from the smart device to the caregivers and/or the medical care team, including all the sensor data, as shown in FIG. 9. Besides the manual mode, an automatic mode is also supported using close-loop control mechanism, as shown in the example flow chart in FIG. 6. Although not depicted in FIG. 6 explicitly, it is meant that mobile application will alert the patient, caregivers, doctor and care team about the adverse conditions, if the patient's conditions had not improved after attempting to automatically improve the environmental factors and/or oxygen supplies, e.g. at the maximum setting of the oxygen supply. The sensor data as collected and processed by the patient's computing device can be displayed to the user numerically and/or graphically (FIG. 10), and sent to the server cloud where they can be shown to the caregivers, doctors and care teams via their dashboard applications or other types of user interface, remotely. An example of the dashboard application is shown in FIG. 10. Other formats for the data plot can also be supported by the dashboard to allow more detail analysis by the care team, e.g. scattered or line plots. In FIG. 10 and FIG. 11, the plots show time variations (x-axis) of the patient's SpO2 measurements (y-axis) and the corresponding activity level, as averaged over each minute. The size of each bubble is proportional to the estimated activity level during the measurement interval. Other variations on the plot style could also be supported, e.g. with size of bubble proportional to the SpO2 levels. Similar plots are used to show the variations in other vital signs, e.g., heart rate.

Outdoor Scenario

When the patient is planning to venture outdoors, mobile application will allow the user to check the air quality of the destination and/or on the route, as appropriate, and advise the patient on the risk level of the planned trip. If the patient has decided to go outdoor, the system will continue to monitor and update the air quality of the patient's current location, e.g., by sending periodic inquiries to the air quality web server, based on the current GPS location: http://www.airnow.gov/index.cfm. Similarly, other environmental factors such as temperature and humidity will also be monitored and updated for the patient, e.g., by inquiring the web server: https://weather.com/weather/today/

It would be possible to have mobile/wearable environmental sensors to measure and monitor the environmental factors, e.g. air quality, temperature and humidity, in the patient's vicinity.

Data Aggregation

The design as described here aggregates various types of data, including but not limited to the list as follows:

Real-time patients vital design data from wearable physiological sensors or bioSensors, e.g., SpO2, heart rate/variability, skin temperature, respiratory rate etc.

Location and motion data from patient's Smartphone, e.g., location, speed of movement, altitude, number of steps & stairs, etc.

Environmental sensor data when available:

Indoor: Air Quality index (Smart Air Purifier), Thermostat with wireless connectivity (Temperature, humidity);

Outdoor: Web sites with temperature, humidity, pollen/pollution/air quality index data for the queried location;

Server data for retrieval, e.g., patients' historical data etc., reference vital sign data for comparison with patient's current measurements;

Data for storage at server, e.g., new vital signs and sensor measurement data (1-3) after filtering & other processing;

Features

The major features that are supported by the health monitoring system can be summarized as follows: Based on the weather (Temperature & humidity) conditions, air quality, and flu infection rate, the health monitoring system can warn the user with respect to the risk level of a certain location, e.g., before the user goes there; obtain thermostat data & control for the patient's comfort indoor; It can monitor the blood oxygen level regularly, alert the user and/or care-taker when it falls below a Threshold, e.g., T1, and increase the oxygen supply level; If the level does not increase after a certain time duration, mobile application alerts the user, care-taker and/or doctor; or If the blood oxygen level continues to drop and becomes lower than another Threshold, e.g., T2, then the health monitoring app would alert the user, care-taker and paramedics; It monitors the blood oxygen level as the user moves, e.g. record the location and speed of the user through the patient's smart watch, smartphone, and/or other wearable devices; it saves the data for analysis and use to predict when the user might experience a problem, based on their location and activity in the future; it warns the user against the location and activity when a problem is predicted; compares the New data with the earlier data to check if there is any deterioration of the patient's condition; If the condition has worsen, it alerts the patient and/or care-taker to schedule an appointment with the doctor; The data as related to location may be further processed and analyzed for use as an indicator of the pollution level at that location, and use to warn other users who are traveling to that area; it alerts patient/caregiver when the Oxygen tank needs a re-fill; provides voice alerts/advice to patient. It can alert patient to take medication and keeping track of the medication record.

Sensor Data Processing

Optimizing for Power Consumption

An optimized system would allow the minimal power consumption at the sensor modules by adapting and sharing the sensor processing and computational load with a host device, e.g., a smartphone, tablet or other devices with processing power. For example, if the power consumption for processing a set of samples X over a certain measurement interval T is Px,c, and for transmitting the samples is Px,t:

(i) Px,t<Px,c=>Transmit the samples to the host device (ii) Px,t>Px,c=>Process the samples on the sensor modules In Case (ii), the results of the processed sensor samples are sent to the host device at an interval greater than T, with a smaller amount of data as compared to (i).

Signal Conditioning

The sensor measurement data would need to be de-noised, e.g. through filtering and/or thresholding. After the measurement sample is de-noised, it is then compared with the nominal or expected value which can be specific to the patient's medical condition. If the new sample is worse than the expected value, then an alert can be generated to inform the caregivers who are connected to the patient, e.g. via a mobile app similar to the one shown in FIG. 11.

Data Processing

The measurement data can be passed through a moving average filter. The output of the moving average filter can be plotted and compared with the reference value, e.g. similar measurements taken at the most recent doctor's office, in the case of vital signs.

The length or duration of the moving average filter can be configured to optimize between de-noising, which is more effective with longer filter length, as a tradeoff to sensitivity of responses to changes.

Calibration

The measurement data from the sensors can be re-calibrated periodically. One way to calibrate the sensors is to compare the filtered measurement data with the vital sign reading taken using a more stable, clinical grade equipment, e.g. by a caregiver or nurse.

The difference in the reading is used by an algorithm to determine if the current measurement would require any attention by the caregivers.

Alert Generation

Besides the comparison with the reference measurement data, the expected normal and abnormal readings would also be taken into account by the algorithm, when an alert is generated for attention at different levels.

An alert is generated based on multiple measurement data or metrics, e.g. if the air quality index shows good air quality, the user does not have abnormally high activity level, and the heart rate is normal, but the SpO2 level is x % lower than the "normal" level for this patient, then an alert would be generated with a suggestion to check the oxygen supply.

In another case, if the SpO2 level is lower than normal while heart rate is higher than normal, with an indication that the user has relatively high activity level, then the alert would be generated with a suggestion for the user to stop the activity and take a rest. After some time "T", e.g. 5 minutes, the algorithm would check the latest conditions, e.g. SpO2 level and heart rate, to determine if a higher level of alert would be necessary, or the current alert can be cleared, in case the vital signs are back to the user's normal value, after the user has stopped the activity.

Monitoring of Other Disease Conditions

While the examples as shown in this document are described for the monitoring of a COPD patient, the monitoring of other diseases can also be done using similar methodologies as described in this document, with inputs from a combination of similar and different types of sensors. For example, monitoring of blood glucose level indicator instead of SpO2 level; and the adjustment of the amount and frequency of insulin injection, instead of flow control on the O2 supply.

In another embodiment, when the sensor measurement data is updated, the caregivers can see the updated information via the connection by a mobile App. The caregivers connecting to the patient can see similar information about the patient.

All examples and conditional language recited herein are intended for educational purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents hereof. Additionally, it is intended that such equivalents include both currently known equivalents as well as equivalents developed in the future, i.e., any elements developed that perform the same function, regardless of structure.

I claim:

1. A personal mobile health management system comprising: a
    mobile application running on a mobile device;
    a personal health/medical record for at least one person including data that is encrypted and stored on said mobile device running said mobile application;
    a plurality of connected mobile devices of caregivers of said person, storing or receiving information related to said personal health/medical record;
    an interface for connecting to a plurality of physically distinct sensors wherein said sensors include vital signs sensors and environmental sensors, and
    said mobile application is further comprised of a plurality of collaboration/synchronization modules comprising:
    a synchronization function to synchronize data included in said personal health/medical record of said person between said mobile application running on said mobile device and said plurality of connected devices of caregivers of said person,
    an update function to receive personal health data updates to said personal health/medical record stored on said mobile device, wherein said update to said personal health/medical record is sent in real-time directly to a plurality of said connected devices of the caregivers of said person, as the said update of the personal health/medical record is stored on the said mobile device,
    an alert function to generate a personalized alert based on the received personal health data of said person, compared to thresholds and conditions configured on the mobile device, and based on escalating alert levels associated with a plurality of mobile devices with higher alert thresholds associated with more serious conditions, wherein the lowest level alert is a reminder,
    a permissions/access management function to add, delete, allow, and enable or deny receiving of data in said personal health/medical record to said plurality of connected devices,
    an integration/synchronization function to exchange health conditions, data, and instructions between said plurality of connected sensors, and devices installed on or connected to said mobile device, and the data received from the plurality of connected devices, and
    an input/message function to enable entry of new messages or reminders into said mobile application running on said mobile device for input into said integration/synchronization function,
    wherein a hub communicates with, or at least one mobile device connected to a hub interfaces with, a plurality of sensors worn by multiple, different people, and collects measurement data for storing personal health/medical records of each person,
    wherein the plurality of connected devices of the plurality of caregivers of said person receive and store the encrypted record data in a distributed architecture and enable access to the encrypted record data by the plurality of connected devices of the plurality of caregivers of said person and enable notifications thereto to be generated from each of the plurality of connected devices of the plurality of caregivers of said person to respective connected devices of other caregivers of the plurality of caregivers when preauthorized by a device with administrator privilege, wherein a caregiver can be one of a person's family member, a community member, a professional caregiving person, a staff at the elderly care facility, a medical assistant, a medical technician, a nurse, a physician, a specialist, an administrator, and/or a social worker, wherein said encrypted record data is transmitted from said mobile device and a first plurality of the connected devices of the plurality of caregivers of said person to a second plurality of the connected devices of the plurality of caregivers of said person directly, without being transmitted through any intermediary server devices.

2. A personal mobile health management system of claim 1 wherein privacy and access configuration can be adapted to different numbers of patients and caregivers, and to ensure the access to an authorized subgroup wherein a member of one group can belong to a different group simultaneously.

3. The personal mobile health management system of claim 1, further comprising connectivity, extension, and synchronization with a distributed computing system on a private or secure computing environment to backup, aggregate data and extend the processing capacity of said personal mobile health system.

4. A method to manage personal health of a person with or without an existing health condition using the mobile health management system of claim 1 further comprising, the entry and updating of vital signs, health related information, proximity information between patient and at least one of connected devices of any members of the care group and other source of potential care, medical record information, appointment information, patient symptom and condition report information, and a plurality of available connected sensors and devices to provision immediate care services to said person, and the automated adjustment of connected environmental and patient devices.

5. The method of claim 4, further comprising the connection/synchronization of at least one other device of a member of a care provider group for said person on said mobile health management system, and said plurality of available connected devices, to provision immediate care services to said person via other connected and synchronized said personal health records on the devices of users/members of said persons care groups.

6. A method to manage personal health of a person with or without an existing health condition using the mobile health management system of claim 1 further comprising, the connection/synchronization of at least one other device of a member of a care provider group for said person on said mobile health management system, and a plurality of available connected devices to provision immediate care services to said person via other connected and synchronized said personal health records on the devices of users/members of said persons care groups.

7. The system of claim 1, further comprising a user privilege hierarchy starting with an administrator first who determines the privilege level of each user in a group and access to certain document and information of any other individual user in the group, next a patient/client's family with a default privilege limited to the access of a client's own document, records and other information and a super client having a highest access privilege for all records of their own clients at a care facility.

8. A personal mobile health management system of claim 1, wherein said personal health record is accessible by said caregiver groups and said caregiver groups are in constant communication with said person via mobile application, which provides a platform for rapid updates to said person's personal health record and said platform allows members to seamlessly contact said person via phone, text and video calls simultaneously within said platform wherein said personal health record system can be connected to the official electronic medical records at the professional providers' system in which said personal health record system has an API interface to various official documents.

9. A personal mobile health management system of claim 1 wherein power, computation and transmission bandwidth consumption of said mobile device is optimized through the distribution and sharing of data processing workload, among sensor modules, mobile devices, and/or hub (gateway), and/or other computing devices.

10. A method to manage personal health of a person with or without an existing health condition using the mobile health management system of claim 1, further comprising:
tracking of patients with Dementia using GPS and Bluetooth connection to the hub,
alerting the caregivers in the group when the patient has wandered too far from home or care center; and
showing the location of the patient to the caregivers in the group.

11. A method to manage personal health of a person with or without an existing health condition using the mobile health management system of claim 1, further comprising:
recording of pain conditions; and
alerting patient in various form wherein text, voice or video messages pre-recorded by family or friends which are scheduled, to manage activities to help reduce pain.

12. A method to manage personal health of a person with or without an existing health condition using the mobile health management system of claim 1, further comprising:
detecting of sleep apnea through the monitoring of blood oxygen concentration SpO2 levels, and
alerting patient or family upon detection.

13. A personal mobile health management system of claim 1 wherein configuration, scheduling of pre-recorded text, voice or video messages by family and friends, as reminders for various purposes.

14. A personal mobile health management system comprising: a
mobile application running on a mobile device;
a personal health/medical record for at least one person including data that is encrypted and stored on said mobile device running said mobile application;
a plurality of connected mobile devices of caregivers of said person, storing or receiving information related to said personal health/medical record;
an interface for connecting to a plurality of physically distinct sensors wherein said sensors include vital signs sensors and environmental sensors, and
said mobile application is further comprised of a plurality of collaboration/synchronization modules comprising:
a synchronization function to synchronize data included in said personal health/medical record of said person between said mobile application running on said mobile device and said plurality of connected devices of caregivers of said person,
an update function to receive personal health data updates to said personal health/medical record stored on said mobile device, wherein said update to said personal health/medical record is sent in real-time directly to a plurality of said connected devices of the caregivers of said person, as the said update of the personal health/medical record is stored on the said mobile device, an alert function to generate a personalized alert based on the received personal health data of said person, compared to thresholds and conditions configured on the mobile device, and based on escalating alert levels associated with a plurality of mobile devices with higher alert thresholds associated with more serious conditions, wherein the lowest level alert is a reminder, a permissions/access management function to add, delete, allow, and enable or deny receiving of data in said personal health/medical record to said plurality of connected devices, an integration/synchronization function to exchange health conditions, data, and instructions between said plurality of connected sensors, and devices installed on or connected to said mobile device, and the data received from the plurality of connected devices, and an input/message function to enable entry of new messages or reminders into said mobile application running on said mobile device for input into said integration/synchronization function, wherein the plurality of connected devices of the plurality of caregivers of said person receive and store the encrypted record data in a distributed architecture and enable access to of the encrypted record data by the plurality of connected devices of the plurality of caregivers of said person and enable notifications thereto to be generated from each of the plurality of connected devices of the plurality of caregivers of said person to respective connected devices of other caregivers of the plurality of caregivers when preauthorized by a device with administrator privilege, wherein a caregiver can be one of a person's family member, a community member, a professional caregiving person, a staff at the elderly care facility, a medical assistant, a medical technician, a nurse, a physician, a specialist, an administrator, and/or a social worker, wherein said encrypted record data is transmitted from said mobile device and a first plurality of the connected devices of the plurality of caregivers of said person to a second plurality of the connected devices of the plurality of caregivers of said person directly, without being transmitted through any intermediary server devices.

15. A personal mobile health management system of claim 14 wherein privacy and access configuration can be adapted to different numbers of patients and caregivers, and to ensure the access to an authorized subgroup wherein a member of one group can belong to a different group simultaneously.

16. The personal mobile health management system of claim 14, further comprising connectivity, extension, and synchronization with a distributed computing system on a private or secure computing environment to backup, aggregate data and extend the processing capacity of said personal mobile health system.

17. A method to manage personal health of a person with or without an existing health condition using the mobile health management system of claim 14 further comprising, the entry and updating of vital signs, health related information, proximity information between patient and at least one of connected devices of any members of the care group and other source of potential care, medical record information, appointment information, patient symptom and condition report information, and a plurality of available connected sensors and devices to provision immediate care services to said person, and the automated adjustment of connected environmental and patient devices.

18. The method of claim 17, further comprising the connection/synchronization of at least one other device of a member of a care provider group for said person on said mobile health management system, and said plurality of available connected devices, to provision immediate care services to said person via other connected and synchronized said personal health records on the devices of users/members of said persons care groups.

19. A method to manage personal health of a person with or without an existing health condition using the mobile health management system of claim 14 further comprising, the connection/synchronization of at least one other device of a member of a care provider group for said person on said mobile health management system, and a plurality of available connected devices to provision immediate care services to said person via other connected and synchronized said personal health records on the devices of users/members of said persons care groups.

20. The system of claim 14, further comprising a user privilege hierarchy starting with an administrator first who determines the privilege level of each user in a group and access to certain document and information of any other individual user in the group, next a patient/client's family with a default privilege limited to the access of a client's own document, records and other information and a super client having a highest access privilege for all records of their own clients at a care facility.

21. A personal mobile health management system of claim 14, wherein said personal health record is accessible by said caregiver groups and said caregiver groups are in constant communication with said person via mobile application, which provides a platform for rapid updates to said person's personal health record and said platform allows members to seamlessly contact said person via phone, text and video calls simultaneously within said platform wherein said personal health record system can be connected to the official electronic medical records at the professional providers' system in which said personal health record system has an API interface to various official documents.

22. A personal mobile health management system of claim 14 wherein power, computation and transmission bandwidth consumption of said mobile device is optimized through the distribution and sharing of data processing workload, among sensor modules, mobile devices, and/or other computing devices.

23. A method to manage personal health of a person with or without an existing health condition using the mobile health management system of claim 14, further comprising:
 tracking of patients with Dementia using GPS and Bluetooth connection to a mobile device,
 alerting the caregivers in the group when the patient has wandered too far from home or care center; and
 showing the location of the patient to the caregivers in the group.

24. A method to manage personal health of a person with or without an existing health condition using the mobile health management system of claim 14, further comprising:
 recording of pain conditions; and
 alerting patient in various form wherein text, voice or video messages pre-recorded by family or friends which are scheduled, to manage activities to help reduce pain.

25. A method to manage personal health of a person with or without an existing health condition using the mobile health management system of claim 14, further comprising:
- detecting of sleep apnea through the monitoring of blood oxygen concentration SpO2 levels, and
- alerting patient or family upon detection.

26. A personal mobile health management system of claim 14 wherein configuration, scheduling of pre-recorded text, voice or video messages by family and friends, as reminders for various purposes.

* * * * *